United States Patent [19]  [11] 4,072,647
Schneider  [45] Feb. 7, 1978

[54] POLYVINYL CHLORIDE PLASTIC COMPOSITIONS

[75] Inventor: Ronald A. Schneider, Richmond, Calif.

[73] Assignee: Chevron Research Company, San Francisco, Calif.

[21] Appl. No.: 696,611

[22] Filed: June 16, 1976

Related U.S. Application Data

[62] Division of Ser. No. 569,508, April 18, 1975, Pat. No. 3,994,959.

[51] Int. Cl.$^2$ ............................................. C08K 5/10
[52] U.S. Cl. ........................... 260/31.8 R; 260/31.8 C
[58] Field of Search ................. 260/31.8 R, 31.8 C, 260/484 P, 535 P, 31.2 R

[56] References Cited

U.S. PATENT DOCUMENTS

| | | | |
|---|---|---|---|
| 2,414,022 | 1/1947 | Clifford et al. | 260/31.8 C |
| 2,886,590 | 5/1959 | Montgomery et al. | 260/484 P |
| 3,431,298 | 3/1969 | Laotome et al. | 260/535 P |

FOREIGN PATENT DOCUMENTS 4,524,021  11/1970  Japan ................................. 260/31.8

*Primary Examiner*—Joseph L. Schofer
*Assistant Examiner*—Peter F. Kulkosky
*Attorney, Agent, or Firm*—D. A. Newell; John Stoner, Jr.; W. Keith Turner

[57] ABSTRACT

3,3'-(3-Methylpentylene-1,5-dioxy) dipropionic acid and esters thereof useful as plasticizers.

1 Claim, No Drawings

POLYVINYL CHLORIDE PLASTIC COMPOSITIONS

This application is a division of Ser. No. 569,508, now U.S. Pat. No. 3,994,959.

BACKGROUND OF THE INVENTION

1. Field of the Invention

The present invention relates to ether acids and esters thereof. More particularly, the invention relates to 3,3'-(3-methylpentylene-1,5-dioxy) dipropionic acid and esters thereof useful as plasticizers.

2. Description of the Prior Art

Common glycols such as ethylene glycol, butylene glycol, and diethylene glycol have been cyanoethylated by reaction with acrylonitrile and then subjected to hydrolysis and alcoholysis to give the corresponding diacids and diesters. See, for instance, Nazarov et al, J. Gen Chem. USSR (Engl. trans.) 24 (1954).

Various ether-diesters have been suggested as synthetic lubricants for applications where ordinary mineral lubricating oils are not entirely satisfactory. See, for instance, U.S. Pat. No. 2,886,590 showing the diester of isoamyl alcohol and 3,6,9-trioxa-1,11-undecanedioic acid.

SUMMARY OF THE INVENTION

In accordance with the present invention there are provided novel ether acids and esters thereof having the formula

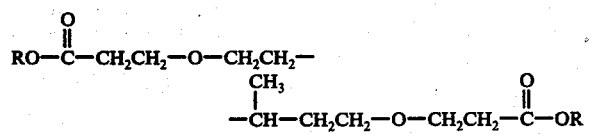

in which the R groups, which may be the same or different, are H or alkyl of 1 to 18 carbon atoms each.

The 3,3'-(3-methylpentylene-1,5-dioxy) dipropionic acid and esters thereof derived from 3-methylpentane-1,5-diol in accordance with the present invention are not only unique in their symmetrical branched-chain structure but are found to have unexpectedly superior properties compared to the ethylene glycol analogs known heretofore.

DESCRIPTION OF THE PREFERRED EMBODIMENTS

The 3-methylpentane-1,5-diol starting material for the ether acids and ester derivatives of the present invention is available from several sources. Conveniently, such materials are obtained by reaction of isobutene and formaldehyde followed by the hydrogenation of the unsaturated diol thus obtained.

The cyanoethylation of 3-methylpentane-1,5-diol with acrylonitrile and hydrolysis and alcoholysis thereof to give the novel acids and esters thereof in accordance with the present invention is readily accomplished. Acrylonitrile is added to the 3-methylpentane-1,5-diol in the presence of alkaline catalyst, for example an aqueous solution of potassium hydroxide, with vigorous stirring at temperatures of from about 20° to 30° C. The dicyanoethyl ether thus obtained is hydrolyzed, for example by the addition of aqueous hydrochloric acid at temperatures of from about 90° to 100° C. Alcoholysis, for example with 2-ethyl-1-hexanol, occurs readily by mixing the diacid and alcohol and heating at reflux temperatures for about 1 hour.

The reaction of 3-methylpentane-1,5-diol in the preparation of the novel ether acids and esters as described above is conveniently illustrated by the following schematic equation and structural formulas:

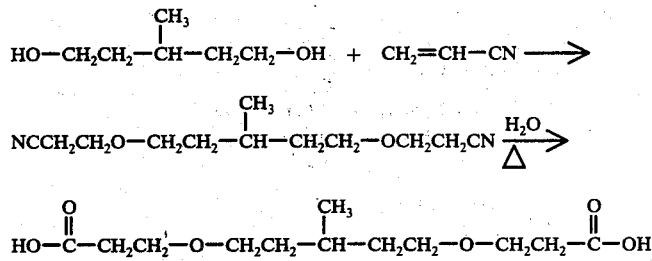

The esters of the ether acids in accordance with the invention are prepared by conventional esterification techniques with the desired alcohols. The alcohols may be aliphatic or cycloaliphatic alcohols of 1 to 18 carbon atoms. However, preferred alcohols are the straight-chain and branched-chain alkyl alcohols of from 4 to 12 carbon atoms, since the esters derived therefrom are particularly suited as plasticizers.

The following examples further illustrate the preparation of the novel ether acids and esters of the invention. Unless otherwise indicated, percentages are on a weight basis.

EXAMPLE 1 — Preparation of 3,3'-(3-Methylpentylene-1,5-dioxy) Dipropionic Acid

In a 3-necked flask equipped with reflux condenser, water bath, thermometer, and mechanical stirrer a solution of 3.12 g. potassium hydroxide in 3.46 g. of water was added to 111.6 g. of 3-methylpentane-1,5-diol (0.94 mol). While the water bath maintained the temperature at 22° to 28° C, acrylonitrile in the amount of 103.3 g (1.88 mols) was added dropwise with vigorous stirring. After about 4 hours the NMR spectrum of the undiluted reaction mixture was consistent with nearly complete conversion to the dicyanoethyl intermediate, peak areas corresponding to 2.9 methyl protons, 5.1 unshifted methylene and methine protons, 3.9 alpha-cyano protons, 7.3 alpha-oxy protons, 0.2 hydroxyl protons, and 0.5 vinyl protons being observed.

To the above dicyanoethyl intermediate was added 275.1 g. of 37.5% hydrochloric acid (103.1 g. HCl) amounting to 2.83 mols. The reaction temperature was maintained at 90° to 100° C for 2 hours with stirring. The reaction mixture turned dark brown and ammonium chloride precipitated, following which the mixture was cooled and allowed to stand overnight. The ammonium chloride precipitate was filtered and washed with ether. The filtrate was extracted twice with ether and the extract was combined with the ether washing from the ammonium chloride precipitate. The combined extract and ether wash was dried with calcium chloride and then with magnesium sulfate and the ether evaporated in a rotary evaporator with the bath temperature gradually increasing to the boiling point of water to give 214 g. (94% of the theoretical) of 3,3'-(3-methylpentylene-1,5-dioxy) dipropionic acid. The crude acid was purified by extracting its ether solution with aqueous base, acidifying, extracting again with ether, and removing the ether first under reduced pressure and finally with a stream of nitrogen. The NMR spectrum consisted of a singlet at 11.46 ppm (2 protons) assigned to the acid proton; triplets of 3.52 ppm (4 protons, J=6 c.p.s.) and 3.42 ppm (4 protons, J=6 c.p.s.), each assigned to one of the pairs of methylene groups next to oxygen; a triplet at 2.50 ppm (4 protons, J=6 c.p.s.) assigned to the methylene group next to carboxyl; a doublet at 0.88 ppm (3 protons, J=5 c.p.s.) assigned to the methyl group; and a broad peak with fine structure centered at 1.5 ppm, assigned to the remaining methylene and methine protons.

EXAMPLE 2 — Preparation of Di(2ethyl-1hexyl) Ester of 3,3'-(3-Methylpentylene-1,5-dioxy) Dipropionic Acid.

In a reaction flask equipped for reflux and azeotropic removal of water, 52.46 g. (0.20 mol) of the ether acid of Example 1, 53.39 g. of 2-ethyl-1-hexanol (0.41 mol), 1.0 g. of sulfonic acid ion exchange resin (Dowex 50W-X8), 100 ml. of benzene, and 2 drops of concentrated sulfuric acid was stirred and heated under reflux for 5 hours. Approximately 7 ml. of water (0.4 mol) was collected. The contents of the reaction flask were then cooled and washed with 20 ml. of 10% aqueous sodium hydroxide. An emulsion was formed and allowed to break overnight. The organic layer was then washed with 20 ml. of water, dried with magnesium sulfate, and filtered. Two drops of acetic acid were added and the benzene evaporated under reduced pressure. Finally the mixture was stripped at 100° C and 40 mm/Hg. About 10 ml. of material distilled overhead at 35° to 40° C at 0.1 to 0.3 mm/Hg. The stripped material had an NMR spectrum corresponding to the di(2-ethyl-1-hexanol) ester.

EXAMPLE 3 — Preparation of Dibutyl Ester of 3,3'-(3-Methylpentylene-1,5-dioxy) Dipropionic Acid Using the procedure of Example 2, 52.46 g. (0.2 mol) of the ether acid of Example 1 and 88.94 g. (1.2 mol) of 1-butanol were reacted and the product worked up to give material of NMR spectrum corresponding to the dibutyl ester of 3,3'-(3-methylpentylene-1,5-dioxy) dipropionic acid.

EXAMPLE 4 — Preparation of Dihexyl Ester of 3,3'-(3-Methylpentylene-1,5-dioxy) Dipropionic Acid Using the procedure of Example 2, 52.46 g. (0.2 mol) of the ether acid of Example 1 and 49.05 g. (0.48 mol) of 1-hexyl alcohol were reacted and the product worked up to give material of NMR spectrum corresponding to the dihexyl ester of 3,3'-(3-methylpentylene-1,5-dioxy) dipropionic acid.

For the purposes of comparison a number of corresponding diesters of the dipropionic acid analogs derived from ethylene glycol were prepared using the procedure of the foregoing examples of the invention.

The above diesters and comparative prior art esters were then incorporated into polyvinyl chloride (PVC) by mixing 39 grams of PVC, 26 grams of ester and 0.65 gram of a commercial barium/cadmium laurate stabilizer. Mixing was accomplished by working the mixture on a rubber mill for 10 minutes at 310° to 320° F. The resulting sheets were then molded (using a conventional PVC mold) into film sheets 4 × 4 inches, in either 10-mil or 70-mil thicknesses. Molding temperature was 330° F. These films were then tested by the methods described in "Plasticizers: Paraplex and Monoplex", Rohm and Hass Co., 1960, pp. 84–89. The following tests were carried out:

1. Volatility — The details of the test are given in the above reference at page 84. In general, the weight loss of a PVC film containing a plasticizer at 90° C for 24 hours is measured and reported as percent weight loss.
2. Soapy Water Extraction — The details of this test are in the above publication, pp. 85–86. In general, the weight loss of a plasticized PVC sample immersed in a 1% aqueous soap solution at 90° C for 24 hours is measured and reported as percent weight loss.
3. Hexane Extraction — The details of the test method are given in the above-cited reference, page 86. In general, the loss in weight of a PVC film containing a plasticizer is determined after 2 hours' immersion in n-hexane at 25° C.
4. Hardness — A slightly modified Shore Durometer Hardness Test, as described on page 87 of the reference, was utilized. In this test, the initial value (0 sec.) of the hardness of a 70-mil sheet is determined using the Shore Durometer with a 2-pound (A) loading.
5. Flex (TF) Temperature — This test was carried out by the well-known method of Clash and Berg [Ind. & Eng. Chem. 34, 1218 (1942)]. In this test, the angular twist of a rectangular test specimen is determined by applying a controlled torque of $5.68 \times 10^3$ dyne-cm to the sample 5 seconds after exposure to various low test temperatures. The temperature at which the angular twist is 200° of arc is then taken as the "flex" (TF) temperature. Flex temperature is defined as "the lower temperature limit of the compound's usefulness as an elastomer".

The results of the above tests on PVC-containing representative examples of the esters of the present invention are given in the Table.

TABLE

| Run No. | Plasticizer | 70 Mil Initial Shore A Hardness | Low Temp. Torsion Modulus | n-Hexane Extraction Wt. Loss | Soapy Water Extraction Wt. Loss | Volatility Wt. Loss |
|---|---|---|---|---|---|---|
| 1 | Dioctyl orthophthalate | 80 | −34° C | 31% | 12% | 9% |
| 2 | Diisodecyl adipate | 82 | −54° C | 39% | 5% | 7% |
| 3 | Di (2-ethylhexyl) ester of ethylene glycol dipropionic adduct | 72 | −55° C | 22% | 36% | 22% |
| 4 | Di (2-ethylhexyl) ester of 3,3'-(methyl- | 81 | −54° C | 33% | 22% | 5% |

TABLE-continued

| Run No. | Plasticizer | 70 Mil Initial Shore A Hardness | Low Temp. Torsion Modulus | n-Hexane Extraction Wt. Loss | Soapy Water Extraction Wt. Loss | Volatility Wt. Loss |
|---|---|---|---|---|---|---|
| | pentylene-1,5-dioxy) dipropionic acid | | | | | |
| 5 | Dihexyl ester of 3,3'-(3-methylpentylene-1,5-dioxy) dipropionic acid | 79 | −54° C | 30% | 32% | 9% |
| 6 | Dihexyl ester of ethylene glycol dipropionic adduct | 77 | −56° C | 21% | 35% | 15% |

The above test results show that the symmetrical 3,3'-(3-methylpentylene-1,5-dioxy) propionic acid and esters thereof in accordance with the present invention possess surprisingly superior properties which distinguish them from other materials known heretofore in the art.

While the character of this invention has been described in detail with illustrative examples, this has been done by way of illustration only and without limitation of the invention. It will be apparent to those skilled in the art that modifications and variations of the illustrative examples may be made in the practice of the invention within the scope of the following claims.

I claim:
1. Polyvinyl chloride plastic compositions containing a compound of the formula

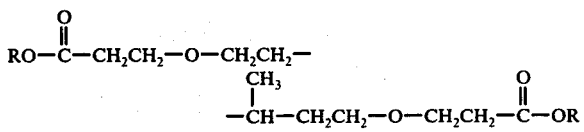

wherein the R groups are primary alkyl of from 4 to 12 carbon atoms, in minor amounts sufficient to impart plasticizing properties.

* * * * *